United States Patent
Paz

(10) Patent No.: US 10,456,332 B2
(45) Date of Patent: Oct. 29, 2019

(54) CONTROLLED DOSAGE FORM-DISPENSING SYSTEM

(71) Applicant: P.C.O.A DEVICES LTD, Tel Aviv (IL)

(72) Inventor: Ilan Paz, Alon Shvut (IL)

(73) Assignee: P.C.O.A. DEVICES LTD., Tel Aviv (IL)

( * ) Notice: Subject to any disclaimer, the term of this patent is extended or adjusted under 35 U.S.C. 154(b) by 3 days.

(21) Appl. No.: 15/321,655

(22) PCT Filed: Jun. 22, 2015

(86) PCT No.: PCT/IL2015/050637
§ 371 (c)(1),
(2) Date: Dec. 22, 2016

(87) PCT Pub. No.: WO2015/198313
PCT Pub. Date: Dec. 30, 2015

(65) Prior Publication Data
US 2017/0135907 A1    May 18, 2017

(30) Foreign Application Priority Data

Jun. 22, 2014   (IL) .......................................... 233295

(51) Int. Cl.
*A61J 7/04* (2006.01)
*A61J 1/03* (2006.01)
(Continued)

(52) U.S. Cl.
CPC .............. *A61J 7/0481* (2013.01); *A61J 1/03* (2013.01); *A61J 7/0076* (2013.01);
(Continued)

(58) Field of Classification Search
None
See application file for complete search history.

(56) References Cited

U.S. PATENT DOCUMENTS

| | | |
|---|---|---|
| 38,343 A | 4/1863 | Tower et al. |
| 708,216 A | 9/1902 | Fowler, Jr. |
| (Continued) | | |

FOREIGN PATENT DOCUMENTS

| | | |
|---|---|---|
| EP | 1721596 B1 | 12/2009 |
| EP | 2301850 | 3/2011 |
| (Continued) | | |

OTHER PUBLICATIONS

PCT/IL2015/050637, International Search Report and Written Opinion, dated Nov. 11, 2015, 10 pages.

*Primary Examiner* — Timothy R Waggoner
(74) *Attorney, Agent, or Firm* — Stoel Rives LLP

(57) ABSTRACT

This invention provides a controlled dosage form-dispensing device, comprising a multi-chamber, bulk medicine storage and distribution unit, wherein said unit is provided with a plurality of individual dosage form-containing storage chambers with respective delivery ports; and a personal medication dispenser comprising a fixed dosage form extracting station comprising a dosage form receiving and extracting mechanism; wherein the medication dispenser is provided with a controller which moves the bulk medicine storage and distribution unit sequentially bringing a respective delivery port of a predetermined chamber into register with the fixed dosage form extracting station such that the dosage form receiving and extracting mechanism extracts and receives only one dosage form at a time. The dispensing device is further provided with at least one portable dosage form-dispensing cassette having a plurality of compartments and a first delivery controller for delivery of a predetermined dosage form from a predetermined compartment of the portable dosage form-dispensing cassette, the at least one portable cassette being releasably attachable to a personal medication dispenser; and a second delivery controller for the controlled delivery of predetermined dosage forms from (Continued)

the multi-chamber, bulk medicine storage and distribution unit to the portable dosage form-dispensing cassette via a conduit in the personal medication dispenser.

15 Claims, 15 Drawing Sheets

(51) Int. Cl.
*A61J 7/00* (2006.01)
*G07F 17/00* (2006.01)
*G06F 19/00* (2018.01)
*G07F 11/00* (2006.01)

(52) U.S. Cl.
CPC ........ *G06F 19/3462* (2013.01); *G07F 11/002* (2013.01); *G07F 17/0092* (2013.01); *A61J 2205/60* (2013.01)

(56) References Cited

U.S. PATENT DOCUMENTS

| | | |
|---|---|---|
| 1,187,634 A | 6/1916 | Lorimer et al. |
| 2,004,243 A | 6/1935 | Hloch |
| 2,470,298 A | 5/1949 | Fields |
| 2,510,712 A | 6/1950 | Olowinski |
| 2,526,749 A | 10/1950 | Hokanson |
| 2,694,641 A | 11/1954 | Atwood |
| 2,740,558 A | 4/1956 | Steele |
| 2,963,200 A | 12/1960 | Miller |
| 3,150,639 A | 9/1964 | Sereda |
| 3,270,918 A | 9/1966 | Burch et al. |
| 3,437,194 A | 4/1969 | Ames et al. |
| RE26,589 E | 5/1969 | Murov et al. |
| 3,505,737 A | 4/1970 | Merolla |
| 3,923,060 A | 12/1975 | Ellinwood, Jr. |
| 4,106,698 A | 8/1978 | Lin |
| 4,114,965 A | 9/1978 | Oye et al. |
| 4,695,954 A | 9/1987 | Rose et al. |
| 4,839,806 A | 6/1989 | Goldfischer et al. |
| 4,872,591 A | 10/1989 | Konopka |
| 4,887,594 A | 12/1989 | Siegel |
| 4,918,690 A | 4/1990 | Markkula, Jr. |
| 5,014,040 A | 5/1991 | Weaver et al. |
| 5,049,125 A | 9/1991 | Accaries et al. |
| 5,110,008 A | 5/1992 | Moulding et al. |
| 5,163,426 A | 11/1992 | Czeisler et al. |
| 5,176,133 A | 1/1993 | Czeisler et al. |
| 5,219,093 A | 6/1993 | Moulding et al. |
| 5,344,043 A | 9/1994 | Moulding et al. |
| 5,431,299 A | 7/1995 | Brewer et al. |
| 5,460,299 A | 10/1995 | Prause |
| 5,475,687 A | 12/1995 | Markkula, Jr. et al. |
| 5,490,610 A | 2/1996 | Pearson |
| 5,524,073 A | 6/1996 | Stambler |
| 5,562,232 A | 10/1996 | Pearson |
| 5,844,888 A | 12/1998 | Markkula, Jr. |
| 5,850,937 A | 12/1998 | Rauche |
| 5,853,244 A | 12/1998 | Hoff et al. |
| 5,955,952 A | 9/1999 | Bergman et al. |
| 6,021,918 A | 2/2000 | Dumont et al. |
| 6,024,247 A | 2/2000 | Birr |
| 6,032,155 A | 2/2000 | De La |
| 6,048,271 A | 4/2000 | Barcelou |
| 6,068,126 A | 5/2000 | Dejonge |
| 6,145,697 A | 11/2000 | Gudish |
| 6,150,942 A | 11/2000 | O'Brien et al. |
| 6,152,364 A | 11/2000 | Schoonen et al. |
| 6,163,736 A | 12/2000 | Halfacre |
| 6,219,587 B1 | 4/2001 | Arlin et al. |
| 6,234,343 B1 | 5/2001 | Papp |
| 6,263,259 B1 | 7/2001 | Bartur |
| 6,304,797 B1 | 10/2001 | Shusterman |
| 6,318,051 B1 | 11/2001 | Preiss |
| 6,327,570 B1 | 12/2001 | Stevens |
| 6,352,200 B1 | 3/2002 | Schoonen et al. |
| 6,415,202 B1 | 7/2002 | Halfacre |
| 6,510,962 B1 | 1/2003 | Lin |
| 6,529,446 B1 | 3/2003 | De La Huerga |
| 6,579,231 B1 | 6/2003 | Phipps |
| 6,601,729 B1 | 8/2003 | Papp |
| 6,604,019 B2 | 8/2003 | Ahlin et al. |
| 6,611,733 B1 * | 8/2003 | De La Huerga ...... A61J 1/1437 700/235 |
| 6,729,327 B2 | 5/2004 | McFarland, Jr. et al. |
| 6,766,219 B1 | 7/2004 | Hasey |
| 6,776,304 B2 | 8/2004 | Liff et al. |
| 6,814,255 B2 | 11/2004 | Liff et al. |
| 6,848,593 B2 | 2/2005 | Papp |
| 6,892,941 B2 | 5/2005 | Rosenblum |
| 6,922,664 B1 | 7/2005 | Fernandez et al. |
| 6,947,900 B2 | 9/2005 | Giordano, III et al. |
| 6,988,634 B2 | 1/2006 | Varis |
| 7,006,894 B2 | 2/2006 | De La |
| 7,030,823 B2 | 4/2006 | Apothéloz et al. |
| 7,044,302 B2 | 5/2006 | Conley |
| 7,051,898 B1 | 5/2006 | Connell |
| 7,084,946 B2 | 8/2006 | Ota et al. |
| 7,178,688 B2 | 2/2007 | Naufel et al. |
| 7,216,776 B2 | 5/2007 | Gelardi |
| 7,216,802 B1 | 5/2007 | De La Huerga |
| 7,231,920 B2 | 6/2007 | Harvey et al. |
| 7,302,311 B2 | 11/2007 | Varis |
| 7,359,765 B2 | 4/2008 | Varvarelis et al. |
| 7,426,475 B1 | 9/2008 | Tangellapally et al. |
| 7,451,761 B2 | 11/2008 | Hickey et al. |
| 7,491,219 B2 | 2/2009 | Steinberg |
| 7,503,081 B2 | 3/2009 | Montgomery |
| 7,624,733 B2 | 12/2009 | Riley et al. |
| 7,624,894 B2 | 12/2009 | Gerold et al. |
| 7,637,079 B2 | 12/2009 | Klingel et al. |
| 7,654,261 B1 | 2/2010 | Rockhold |
| 7,665,811 B2 | 2/2010 | Johanning |
| 7,677,941 B2 | 3/2010 | Koyama |
| 7,692,195 B2 | 4/2010 | Namose |
| 7,704,236 B2 | 4/2010 | Denolly |
| 7,727,469 B2 | 6/2010 | Takahashi et al. |
| 7,743,923 B2 | 6/2010 | Conley |
| 7,766,365 B2 | 8/2010 | Darling, III |
| 7,771,984 B2 | 8/2010 | Dzekunov et al. |
| 7,787,986 B2 | 8/2010 | Pinney et al. |
| 7,828,147 B2 | 11/2010 | Caracciolo et al. |
| 7,844,362 B2 | 11/2010 | Handfield et al. |
| 7,860,724 B2 | 12/2010 | Chudy et al. |
| 7,865,263 B2 | 1/2011 | Spano, Jr. et al. |
| 7,885,725 B2 | 2/2011 | Dunn |
| 7,896,192 B2 | 3/2011 | Conley et al. |
| 7,930,056 B2 | 4/2011 | Fernandez |
| 7,932,832 B2 | 4/2011 | Hayashi |
| 7,934,355 B2 | 5/2011 | Strub et al. |
| 7,946,483 B2 | 5/2011 | Miller et al. |
| 7,978,083 B2 | 7/2011 | Melker et al. |
| 7,988,016 B2 | 8/2011 | Klein et al. |
| 7,996,106 B2 | 8/2011 | Ervin |
| 7,999,987 B2 | 8/2011 | Namose |
| 8,006,903 B2 | 8/2011 | Braun |
| 8,015,417 B2 | 9/2011 | Kato et al. |
| 8,027,748 B2 | 9/2011 | Handfield et al. |
| 8,032,397 B2 | 10/2011 | Lawless |
| 8,065,035 B2 | 11/2011 | Ross et al. |
| 8,073,563 B2 | 12/2011 | Vahlberg et al. |
| 8,090,473 B2 | 1/2012 | Higham |
| 8,103,346 B2 | 1/2012 | Mass et al. |
| 8,103,379 B2 | 1/2012 | Biba et al. |
| 8,112,942 B2 | 2/2012 | Bohm et al. |
| 8,118,222 B2 | 2/2012 | Barcelou |
| 8,126,590 B2 | 2/2012 | Vahlberg et al. |
| 8,135,497 B2 | 3/2012 | Joslyn |
| 8,140,186 B2 | 3/2012 | Vahlberg et al. |
| 8,145,353 B1 | 3/2012 | Cotner |
| 8,162,690 B2 | 4/2012 | Smith |
| 8,195,329 B2 | 6/2012 | Pinney et al. |
| 8,265,757 B2 | 9/2012 | Mass et al. |
| 8,266,447 B2 | 9/2012 | Völkening et al. |

(56) References Cited

U.S. PATENT DOCUMENTS

| | | | |
|---|---|---|---|
| 8,280,550 B2 | 10/2012 | Levy et al. | |
| 8,343,434 B2 | 1/2013 | Hyde et al. | |
| 8,386,073 B2* | 2/2013 | Kim | B65B 5/103 |
| | | | 221/167 |
| 8,390,761 B2 | 3/2013 | Oda | |
| 8,395,314 B2 | 3/2013 | Yamamoto et al. | |
| 8,417,378 B2 | 4/2013 | Joslyn | |
| 8,468,031 B2 | 6/2013 | Jung et al. | |
| 8,478,604 B2 | 7/2013 | Henderson et al. | |
| 8,494,878 B2 | 7/2013 | Stevens | |
| 8,504,197 B2 | 8/2013 | Farr | |
| 8,554,365 B2 | 10/2013 | Thomas et al. | |
| 8,587,427 B2 | 11/2013 | Lalonde et al. | |
| 8,615,971 B2 | 12/2013 | Freudelsperger | |
| 8,626,342 B2 | 1/2014 | Williams | |
| 8,672,879 B2 | 3/2014 | Grant et al. | |
| 8,725,291 B2 | 5/2014 | Czaja et al. | |
| 8,787,555 B2 | 7/2014 | Gonen et al. | |
| 8,827,112 B2* | 9/2014 | Yuyama | A61J 7/02 |
| | | | 221/237 |
| 8,926,526 B2 | 1/2015 | Shuck | |
| 8,930,207 B2 | 1/2015 | Keravich et al. | |
| 8,954,190 B2 | 2/2015 | Braunstein | |
| 9,014,847 B2 | 4/2015 | Dunn | |
| 9,031,690 B2 | 5/2015 | Cotner | |
| 9,037,616 B2 | 5/2015 | Bessette | |
| 9,043,012 B2 | 5/2015 | Davey et al. | |
| 9,098,983 B2 | 8/2015 | Rahilly | |
| 9,107,571 B2 | 8/2015 | Strauss et al. | |
| 9,111,408 B2 | 8/2015 | Biba et al. | |
| 9,185,501 B2 | 11/2015 | Pai | |
| 9,211,498 B2 | 12/2015 | Akdogan et al. | |
| 9,235,689 B2 | 1/2016 | Ervin | |
| 9,242,043 B2 | 1/2016 | Ludolph | |
| 9,245,305 B2 | 1/2016 | Wellington et al. | |
| 9,358,499 B2 | 6/2016 | Akdogan et al. | |
| 9,358,500 B2 | 6/2016 | Akdogan et al. | |
| 9,361,748 B2 | 6/2016 | Cunningham et al. | |
| 9,381,311 B2 | 7/2016 | Holakovsky et al. | |
| 9,387,153 B1 | 7/2016 | Mazur | |
| 9,400,873 B2 | 7/2016 | Kamen et al. | |
| 9,443,062 B2 | 9/2016 | Long et al. | |
| 9,463,412 B2 | 10/2016 | Akdogan et al. | |
| 9,465,919 B2 | 10/2016 | Kamen et al. | |
| 9,475,633 B2* | 10/2016 | Hoover | A61J 7/0069 |
| 9,508,935 B2 | 11/2016 | Watanabe | |
| 9,550,031 B2 | 1/2017 | Van Sickle et al. | |
| 9,561,324 B2 | 2/2017 | Estes | |
| 9,600,635 B2 | 3/2017 | Czaja | |
| 9,665,689 B2 | 5/2017 | O'Brien et al. | |
| 9,675,523 B2 | 6/2017 | Ducatt et al. | |
| 9,707,358 B2 | 7/2017 | Eggert et al. | |
| 9,730,005 B2 | 8/2017 | Pai | |
| 2002/0026332 A1 | 2/2002 | Snowden et al. | |
| 2002/0034978 A1 | 3/2002 | Legge et al. | |
| 2002/0070227 A1 | 6/2002 | Ferruccio | |
| 2002/0088825 A1 | 7/2002 | Laverdure | |
| 2002/0165641 A1 | 11/2002 | Manalang et al. | |
| 2003/0029880 A1 | 2/2003 | Hunts | |
| 2003/0042167 A1 | 3/2003 | Balz et al. | |
| 2003/0115082 A1 | 6/2003 | Jacobsen et al. | |
| 2003/0127463 A1* | 7/2003 | Varis | A61J 7/0084 |
| | | | 221/2 |
| 2003/0216625 A1 | 11/2003 | Phipps | |
| 2004/0019502 A1 | 1/2004 | Leaman | |
| 2004/0039481 A1 | 2/2004 | De La Huergra | |
| 2004/0045858 A1 | 3/2004 | Harrold | |
| 2004/0073454 A1 | 4/2004 | Urquhart et al. | |
| 2004/0077937 A1 | 4/2004 | Yarden | |
| 2004/0139000 A1 | 7/2004 | Amos | |
| 2004/0158350 A1* | 8/2004 | Ostergaard | A61J 7/0481 |
| | | | 700/231 |
| 2004/0158507 A1 | 8/2004 | Meek et al. | |
| 2004/0244794 A1 | 12/2004 | Richards | |
| 2004/0249250 A1 | 12/2004 | McGee et al. | |
| 2005/0043965 A1 | 2/2005 | Heller et al. | |
| 2005/0211768 A1 | 9/2005 | Stillman | |
| 2005/0258066 A1* | 11/2005 | Conley | A61J 7/0472 |
| | | | 206/538 |
| 2006/0104765 A1 | 5/2006 | Yuyama | |
| 2006/0125356 A1 | 6/2006 | Meek, Jr. et al. | |
| 2006/0154642 A1 | 7/2006 | Scannell, Jr. | |
| 2006/0184524 A1 | 8/2006 | Pollanz | |
| 2006/0194075 A1 | 8/2006 | Miyamoto et al. | |
| 2006/0204922 A1 | 9/2006 | Anderson et al. | |
| 2006/0259188 A1* | 11/2006 | Berg | A61J 7/0084 |
| | | | 700/231 |
| 2007/0042488 A1 | 2/2007 | Bornemann | |
| 2007/0051072 A1 | 3/2007 | Lai | |
| 2007/0093932 A1* | 4/2007 | Abdulhay | A61J 7/0084 |
| | | | 700/231 |
| 2007/0104731 A1 | 5/2007 | Kelleher et al. | |
| 2007/0185614 A1 | 8/2007 | Bain | |
| 2007/0197978 A1 | 8/2007 | Wortham | |
| 2007/0213877 A1 | 9/2007 | Hart et al. | |
| 2007/0222554 A1 | 9/2007 | Hart | |
| 2007/0261985 A1 | 11/2007 | Allen | |
| 2008/0004507 A1 | 1/2008 | Williams et al. | |
| 2008/0035520 A1 | 2/2008 | Caracciolo et al. | |
| 2008/0164275 A1 | 7/2008 | Poutiatine et al. | |
| 2008/0179387 A1 | 7/2008 | Cantlay et al. | |
| 2008/0189173 A1 | 8/2008 | Bakar et al. | |
| 2008/0251551 A1 | 10/2008 | Huber et al. | |
| 2008/0257904 A1 | 10/2008 | Schiff | |
| 2008/0283542 A1 | 11/2008 | Lanka et al. | |
| 2009/0024248 A1 | 1/2009 | Hodson | |
| 2009/0055223 A1 | 2/2009 | Jung et al. | |
| 2009/0073356 A1 | 3/2009 | Moriyama et al. | |
| 2009/0079335 A1 | 3/2009 | Mitsuya et al. | |
| 2009/0134368 A1 | 5/2009 | Shibatani et al. | |
| 2009/0135120 A1 | 5/2009 | Shibatani | |
| 2009/0135349 A1 | 5/2009 | Shibatani et al. | |
| 2009/0152514 A1 | 6/2009 | Takiguchi et al. | |
| 2009/0152516 A1 | 6/2009 | Shibatani et al. | |
| 2009/0152518 A1 | 6/2009 | Takiguchi et al. | |
| 2009/0185114 A1 | 7/2009 | Takiguchi | |
| 2009/0189128 A1 | 7/2009 | Takiguchi et al. | |
| 2009/0230164 A1 | 9/2009 | Freeman | |
| 2009/0240528 A1 | 9/2009 | Bluth | |
| 2009/0250485 A1 | 10/2009 | Klingel | |
| 2009/0281657 A1* | 11/2009 | Gak | A61J 7/0481 |
| | | | 700/242 |
| 2009/0302048 A1 | 12/2009 | Nobilet et al. | |
| 2010/0005445 A1 | 1/2010 | Argue et al. | |
| 2010/0016746 A1 | 1/2010 | Hampton et al. | |
| 2010/0041056 A1 | 2/2010 | Kinnon et al. | |
| 2010/0205009 A1 | 8/2010 | Kostoff | |
| 2010/0237338 A1 | 9/2010 | Yamamoto et al. | |
| 2010/0250697 A1 | 9/2010 | Hansen et al. | |
| 2010/0294927 A1 | 11/2010 | Nelson et al. | |
| 2010/0312137 A1 | 12/2010 | Gilmour et al. | |
| 2011/0014351 A1 | 1/2011 | Reider et al. | |
| 2011/0130635 A1 | 6/2011 | Ross | |
| 2011/0173028 A1 | 7/2011 | Bond | |
| 2011/0190635 A1 | 8/2011 | Bosler | |
| 2011/0270442 A1 | 11/2011 | Conley et al. | |
| 2012/0003928 A1 | 1/2012 | Geboers | |
| 2012/0066097 A1 | 3/2012 | Amos | |
| 2012/0259456 A1* | 10/2012 | Saltsov | A61J 7/0076 |
| | | | 700/236 |
| 2013/0018356 A1 | 1/2013 | Prince | |
| 2013/0046276 A1 | 2/2013 | Mernoe et al. | |
| 2013/0070090 A1 | 3/2013 | Bufalini et al. | |
| 2013/0090744 A1 | 4/2013 | Tran | |
| 2013/0104284 A1 | 5/2013 | Kantrowitz et al. | |
| 2013/0173302 A1 | 7/2013 | Hyde et al. | |
| 2013/0231954 A1 | 9/2013 | Bryant | |
| 2013/0234855 A1 | 9/2013 | Knighton | |
| 2013/0290115 A1 | 10/2013 | Leoni et al. | |
| 2013/0297068 A1 | 11/2013 | Marshall | |
| 2013/0310664 A1 | 11/2013 | Kozloski et al. | |
| 2013/0317835 A1 | 11/2013 | Mathew | |
| 2014/0177825 A1 | 6/2014 | Mattsson et al. | |
| 2014/0241838 A1 | 8/2014 | Beck et al. | |

(56) References Cited

U.S. PATENT DOCUMENTS

| | | |
|---|---|---|
| 2014/0241839 A1 | 8/2014 | Beck et al. |
| 2014/0244033 A1 | 8/2014 | Ucer et al. |
| 2014/0277136 A1 | 9/2014 | Stein |
| 2014/0318078 A1* | 10/2014 | Kondo .................. B65B 57/10 53/54 |
| 2014/0320289 A1 | 10/2014 | Raichman |
| 2015/0057574 A1 | 2/2015 | Baym et al. |
| 2015/0058041 A1 | 2/2015 | Ervin |
| 2015/0081330 A1 | 3/2015 | Mann et al. |
| 2015/0083742 A1 | 3/2015 | Choi et al. |
| 2015/0148943 A1 | 5/2015 | Sullivan |
| 2015/0191294 A1 | 7/2015 | Paz |
| 2015/0374441 A1 | 12/2015 | Machado et al. |
| 2016/0012445 A1 | 1/2016 | Villa-Real |
| 2016/0066855 A1 | 3/2016 | Hyde et al. |
| 2016/0089303 A1 | 3/2016 | Latorraca et al. |
| 2016/0089491 A1 | 3/2016 | Smith |
| 2016/0158465 A1 | 6/2016 | Coats et al. |
| 2016/0210439 A1 | 7/2016 | Hartlaub et al. |
| 2016/0259183 A1 | 9/2016 | Rayner |
| 2016/0267229 A1 | 9/2016 | High et al. |
| 2016/0283691 A1 | 9/2016 | Ali |
| 2016/0314272 A1 | 10/2016 | Braustein |
| 2016/0346056 A1 | 12/2016 | Demers et al. |
| 2016/0350500 A1 | 12/2016 | Benja-Athon |
| 2016/0354284 A1 | 12/2016 | Liou et al. |
| 2016/0367188 A1 | 12/2016 | Malik et al. |
| 2016/0367421 A1 | 12/2016 | Ead |
| 2016/0374902 A1 | 12/2016 | Govindasamy |
| 2017/0020785 A1 | 1/2017 | McCullough |
| 2017/0032092 A1 | 2/2017 | Mink et al. |
| 2017/0043896 A1 | 2/2017 | Fernandez |
| 2017/0231870 A1 | 8/2017 | Stachler et al. |

FOREIGN PATENT DOCUMENTS

| | | |
|---|---|---|
| JP | 2006052019 A | 2/2006 |
| WO | 1992020455 A1 | 11/1992 |
| WO | 1996013790 A1 | 5/1996 |
| WO | 199708078 A1 | 3/1997 |
| WO | 199910830 A1 | 3/1999 |
| WO | 2000064754 A1 | 11/2000 |
| WO | 2001067345 A1 | 9/2001 |
| WO | 2001076460 A2 | 10/2001 |
| WO | 2002071955 A2 | 9/2002 |
| WO | 2002095645 A1 | 11/2002 |
| WO | 2003015838 A2 | 2/2003 |
| WO | 2003040686 A2 | 5/2003 |
| WO | 2003046695 A2 | 6/2003 |
| WO | 2005109119 A1 | 11/2005 |
| WO | 2007070570 A2 | 6/2007 |
| WO | 2009036316 A1 | 3/2009 |
| WO | 2010008377 A1 | 1/2010 |
| WO | 2011002319 A2 | 1/2011 |
| WO | 2011055040 A1 | 5/2011 |
| WO | 2011151056 A1 | 12/2011 |
| WO | 2012040528 A1 | 3/2012 |
| WO | 2012066580 A2 | 5/2012 |
| WO | 2012069896 A1 | 5/2012 |
| WO | 2012098248 A2 | 7/2012 |
| WO | 2012098249 A1 | 7/2012 |
| WO | 2014059310 A2 | 4/2014 |
| WO | 2014144548 A2 | 9/2014 |
| WO | 2015016375 A1 | 2/2015 |
| WO | 2015113149 A1 | 8/2015 |
| WO | 2015117049 A2 | 8/2015 |
| WO | 2015196293 A1 | 12/2015 |
| WO | 2016030902 A1 | 3/2016 |
| WO | 2016036566 A1 | 3/2016 |
| WO | 2016090315 | 6/2016 |
| WO | 2016103256 A1 | 6/2016 |
| WO | 2016137186 A1 | 9/2016 |
| WO | 2016155970 A1 | 10/2016 |
| WO | 2016181014 A1 | 11/2016 |
| WO | 2016189497 A1 | 12/2016 |
| WO | 2016196102 A1 | 12/2016 |
| WO | 2017055728 A2 | 4/2017 |

* cited by examiner

CONTROLLED DOSAGE FORM-DISPENSING SYSTEM

RELATED APPLICATIONS

This application is a United States National Phase entry of of International Application No. PCT/IL2015/050637 filed Jun. 22, 2015, which claims the benefit of Israel Application No. 233295, filed on Jun. 22, 2014. The entire contents of both of the foregoing applications are hereby incorporated by reference herein.

FIELD OF THE INVENTION

The present invention relates to the field of controlled medication administration. Particularly, the present invention relates to medication dispensers. More particularly, the present invention relates to a receptacle for containing and dispensing solid medicinal dosage forms. Even more particularly, the present invention relates to a medication dispenser having a multi-chamber, bulk, medicine storage and distribution unit for administering dosage forms.

BACKGROUND OF THE INVENTION

Poor medication adherence contributes to an estimated over $290 billion in unnecessary health care costs, 89,000 deaths and 2.4 million unnecessary hospitalizations per year for the over 150 million Americans with at least one chronic condition. Moreover, more than 50% of prescriptions are not completed correctly, and for long-term patients with complex regimens, adherence has been reported to be below 30%. (New England Healthcare Institute, *Medication Adherence and Care Teams: A Call for Demonstration Projects*, September 2010.)

There exist prior art devices for containing and dispensing solid medicinal pills and other solid dosage forms, however, they all have difficulties or drawbacks associated with them.

US 2009/0281657 to Gak et al. discloses a personal medication reminder and dispensing device having a programmable personal medicine container with an alarm for reminding a person to take or administer medicine in accordance with a medication regimen. In this patent the dispenser has stationary bulk pill containers which have to be filled manually from a pharmacy supplied container. Each bulk container has its own pill dispensing apparatus.

Additional prior art documents that describe medication dispensers include: US 2012055948, US2006097000, US 2003127463, US 2006180900 and US 2008300719, however, none of the above patent documents solve the problems associated with medication adherence in the inventive manner in which the present invention does.

Accordingly, it is an object of the present invention to obviate the problems mentioned above and other associated problems by providing a controlled dosage form-dispensing system comprising both a personal and portable device, that may be programmed only by authorized persons, in order to dispense the correct number of dosage forms, such as pills at the desired time on the desired day, to accomplish these objectives. The term "personal" as used herein is intended to denote that the device is individualized to the specific user for his personal use, as will be most convenient and appropriate for the user, for example, at home or in a care center such as a hospital or health care facility.

Additionally, it is an object of the present invention to provide a controlled dosage form-dispensing system for containing and dispensing solid medicinal dosage forms, such as tablets, caplets, capsules and other solid forms in hospitals and nursing facilities as well as at home.

It is yet another object of the present invention to provide a controlled dosage form-dispensing system for containing and dispensing solid medicinal dosage forms, one or more at a time.

It is another object of the present invention to provide a controlled pill-dispensing system that is fully automated, thereby reducing errors in adhering to a medication regimen, and thereby avoid the dangers associated with such errors.

It is yet another object of the present invention to provide a controlled pill-dispensing system for containing and dispensing solid medicinal dosage forms that is easy and inexpensive to manufacture, and simple to use.

It is yet another object of the present invention to provide a lockable bulk chamber supplied by the pharmacy and receivable by the personal dispenser and openable only by the dispenser.

Additional objects and advantages of the invention will become apparent as the description proceeds.

SUMMARY OF THE INVENTION

In one embodiment, this invention provides a controlled dosage form-dispensing device, comprising:
 a. a multi-chamber, bulk medicine storage and distribution unit, wherein said unit is provided with a plurality of individual dosage form-containing storage chambers with respective delivery ports; and
 b. a personal medication dispenser comprising a fixed dosage form extracting station comprising a dosage form receiving and extracting mechanism;
wherein said medication dispenser is provided with a controller which moves said bulk medicine storage and distribution unit, sequentially bringing said respective delivery port of a predetermined chamber into register with said fixed dosage form extracting station such that said dosage form receiving and extracting mechanism extracts and receives only one dosage form at a time.

In some aspects, the controlled dosage form-dispensing device allows for the regulated access of the user to the dosage forms/medicinal products located within the device.

In some aspects, the devices of this invention promote the bulk medicine storage and distribution unit being moved about an axis to bring same (via its respective delivery ports) into register with the extracting unit such that only one dosage form at a time is released. In some embodiments, the sequential delivery can be quite fast, so that although the dosage forms are delivered one at a time, rapid administration is accommodated.

In some aspects, the device is suitable for use with any solid dosage form.

In one embodiment of the present invention there is provided a controlled dosage form-dispensing system, comprising:
 a. a multi-chamber, bulk medicine storage and distribution unit, wherein said unit is provided with a plurality of individual dosage form-containing chambers; and
 b. a portable personal medication dispenser incorporating said unit;
wherein each of said pill storage chambers is provided with a delivery port, and said medication dispenser is provided with means for moving said unit to sequentially bring a delivery port of a predetermined chamber into register with a fixed pill extracting station comprising a pill receiving and extracting mechanism, said mechanism extracting and receiving only one pill at a time.

In some aspects, each chamber is sized to receive and engage individual drug distributor issued, pre-packaged pill storage containers.

In some aspects, each chamber is sized to receive and engage individual drug distributor issued, pre-packaged dosage form storage containers.

In some embodiments, individual drug distributor issued, prepackaged dosage form storage containers are locked once filled, and are unlockable only within said personal medication dispenser.

In some embodiments, the controlled dosage form-dispensing device further comprises:
 a. at least one portable dosage form-dispensing cassette having a plurality of compartments and a first delivery controller for delivery of a predetermined dosage form from a predetermined compartment of said portable dosage form-dispensing cassette, said at least one portable cassette being releasably attachable to a personal medication dispenser; and
 b. a second delivery controller for the controlled delivery of predetermined dosage forms from said multi-chamber, bulk medicine storage and distribution unit to said portable dosage form-dispensing cassette via a conduit in said personal medication dispenser.

In some aspects, said system further comprises
 a. at least one portable pill-dispensing cassette having a plurality of compartments and means for controlled delivery of a predetermined pill from a predetermined compartment of said cassette, said at least one portable cassette being releasably attachable to said personal medication dispenser; and
 b. means for the controlled delivery of predetermined dosage forms from said unit to said portable cassette via said medication dispenser.

In some embodiments of the present invention there is provided a controlled dosage form-dispensing system comprising:
 a. a multi-chamber, bulk medicine storage and distribution unit, wherein said unit is provided with a plurality of individual chambers, each chamber being sized to receive and engage individual drug distributor issued, pre-packaged pill storage containers;
 b. a home (or personal) medication dispenser incorporating said unit;
 c. at least one portable pill-dispensing cassette having a plurality of compartments and means for controlled delivery of a predetermined pill from a predetermined compartment of said cassette, said at least one portable cassette being releasably attachable to said home (or personal) medication dispenser; and
 d. means for the controlled delivery of predetermined pills from said unit to said portable cassette via said medication dispenser;
wherein each of said pill storage containers is provided with a delivery port, and said medication dispenser is provided with means for moving said unit to sequentially bring a delivery port of a predetermined compartment and its chamber into register with a fixed pill extracting station comprising a pill receiving and extracting mechanism, said mechanism extracting and receiving only one pill at a time.

In some embodiments, said individual prepackaged pill storage containers are locked once filled, and are unlockable only within said medication dispenser.

In some embodiments, each chamber is sized to receive and engage individual drug distributor issued, pre-packaged dosage form storage containers.

In some embodiments, the device is provided with a portable pocket dispensing unit into which said portable dosage form-dispensing cassette is inserted. According to this aspect, and in some embodiments, the portable pocket dispensing unit is in wireless communication with a network.

According to this aspect, and in some embodiments, the device dispenses drugs and provides any one of an audio, visual and radio communication signal to a user according to the information received from said RFID tag.

In some embodiments, the portable dosage form-dispensing cassette is disposable.

In some embodiments, the personal medication dispenser comprises a rotator which rotates said multi-chamber, bulk medicine storage and distribution unit. According to this aspect, the rotator may be constructed of any appropriate material and of any appropriate structure, which can be manually or motor-operated, capable of rotating the multi-chamber bulk medicine storage and distribution unit, as described, and exemplified herein and as will be apparent to the skilled artisan.

In some embodiments said medication dispenser is provided with any of many means for rotating said unit.

In some embodiments each chamber or each container contains a multiplicity of a single type of dosage form.

In some aspects, the device is provided with a portable pocket dispensing unit into which said portable dosage form-dispensing cassette is inserted.

In some embodiments, the portable pocket dispensing unit is in wireless communication with a network. In some embodiments, the device dispenses drugs and provides any one of an audio, visual and radio communication signal to a user according to the information received from said RFID tag.

In some embodiments, the portable dosage form-dispensing cassette is disposable.

In some embodiments, the personal medication dispenser comprises a rotator which rotates said multi-chamber, bulk medicine storage and distribution unit.

In some aspects, the system is provided with a portable pocket dispensing unit into which said portable cassette is inserted.

In other embodiments, individual prepackaged pill storage containers are locked once filled and are unlockable only within the medication dispenser. Each container contains, in some embodiments, a multiplicity of a single type of pill or in some embodiments, multiple dosage forms which may be of various types.

Thus, in some embodiments, in order to secure the dosage forms and ensure that same are only delivered to the intended patient, said containers are locked during delivery and transport.

Thereafter, they are locked into their respective chambers in the bulk medicine storage and distribution unit, and in some embodiments, are extractable only by means of the stationary pill receiving and extracting mechanism.

The medicine storage and distribution unit is pin some embodiments, removable from the dispenser for external prepackaging of drug distributor issued dosage forms.

In some aspects, the personal medication dispenser is preferably further provided with a channel for the controlled delivery of predetermined dosage forms from the unit to a dispensing receptacle for receiving a pill from the channel and dispensing the same.

In some aspect, the personal medication dispenser comprises a conduit for the controlled delivery of predetermined dosage forms from said multi-chamber, bulk medicine storage and distribution unit to a dispensing receptacle for receiving a pill from said channel and dispensing the same.

In some aspects, the personal medication dispenser is in communication with said portable cassette, said cassette having an RFID (radio frequency identification) tag, or other form of bar code, for storing information related to the cassette contents.

In some embodiments, the system is also provided with a pocket dispensing unit into which the portable cassette is inserted.

In some aspects, the system dispenses drugs and provides any one of an audio, visual and radio communication signal to a user according to the information received from the RFID tag.

In other embodiments, the individual chambers, the portable pill dispensing cassette and the removable medicine storage and distribution unit are each optionally disposable.

In other embodiments, the personal medication dispenser is sized such that it is movable and can be moved from one location to another simply by picking it up and carrying it to the desired location.

In other embodiments, the personal medication dispenser may be operated by a home care personnel or the user.

In other embodiments, each of the home or personal medication dispenser and the pocket dispensing unit are in wireless communication with a network, such as a cloud-based network To accomplish the above and related objects, the invention may be embodied in the form illustrated in the accompanying drawings. With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description taken with the attached figures making apparent to those skilled in the art how the several forms of the invention may be embodied in practice.

DETAILED DESCRIPTION OF THE PREFERRED EMBODIMENTS

Figure 1A:
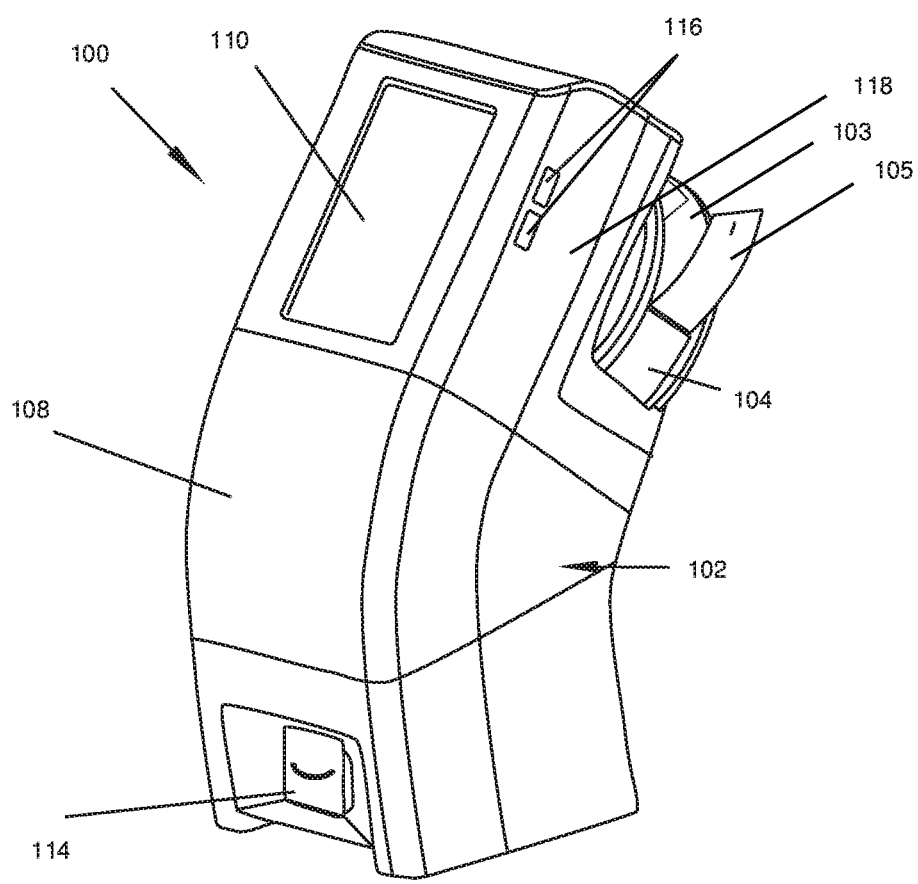
FIG. 1a shows a front perspective view of an assembled controlled dosage form-dispensing system of the present invention.
Figure 2A:
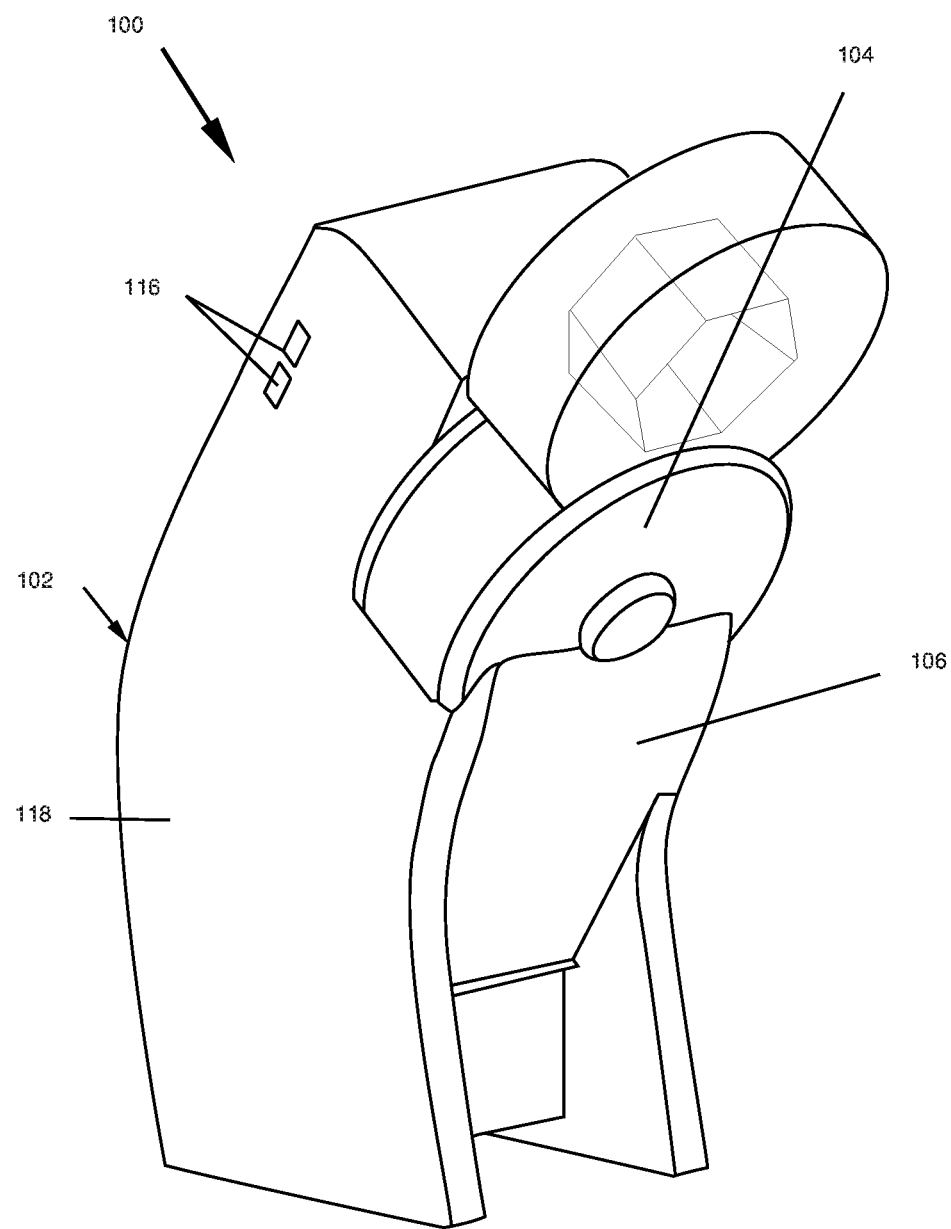
FIG. 2a shows a back perspective view of a controlled dosage form-dispensing system of the present invention.

An embodiment of a controlled dosage form-dispensing system of the present invention is shown assembled in a front perspective view in FIG. 1a and in a back perspective view in FIG. 2a, and is generally designated by numeral (100). System (100) comprises a home medication dispenser (102) for accommodating a medicine storage and distribution unit (104) at the back (106) of dispenser (102). The front (108) of dispenser (102) comprises a display screen (110). A door (105) for filling the container is also provided.

Figure 2B:
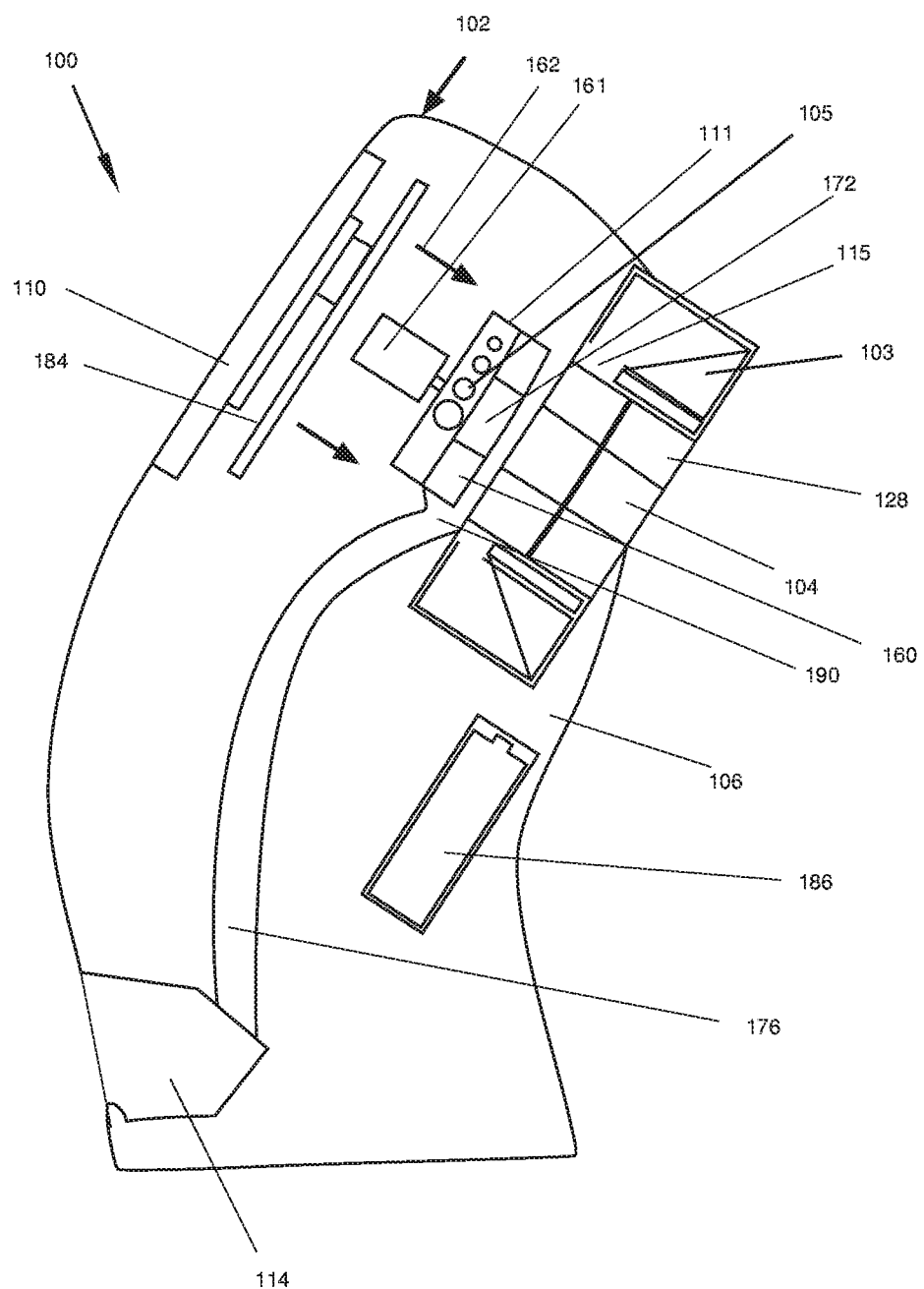
FIG. 2b shows schematically, a personal medication dispenser and its components, longitudinally cross sectioned, such that the internal components of a dispenser are seen.

Referring to FIG. 2b, controlled dosage form-dispensing system (100) is shown schematically, longitudinally cross-sectioned, such that dispenser (102) and its internal components are seen. When storage and distribution unit (104) is installed within dispenser (102), driving and rotating mechanism (160) shifts in the direction of arrows (162) such that shaft (172) is disposed within opening (128) of storage and distribution unit (104). Preferably, the shifting of driving and rotating mechanism (160) is automated, however the user may selectively shift driving and rotating mechanism (160) manually.

Figure 2C:
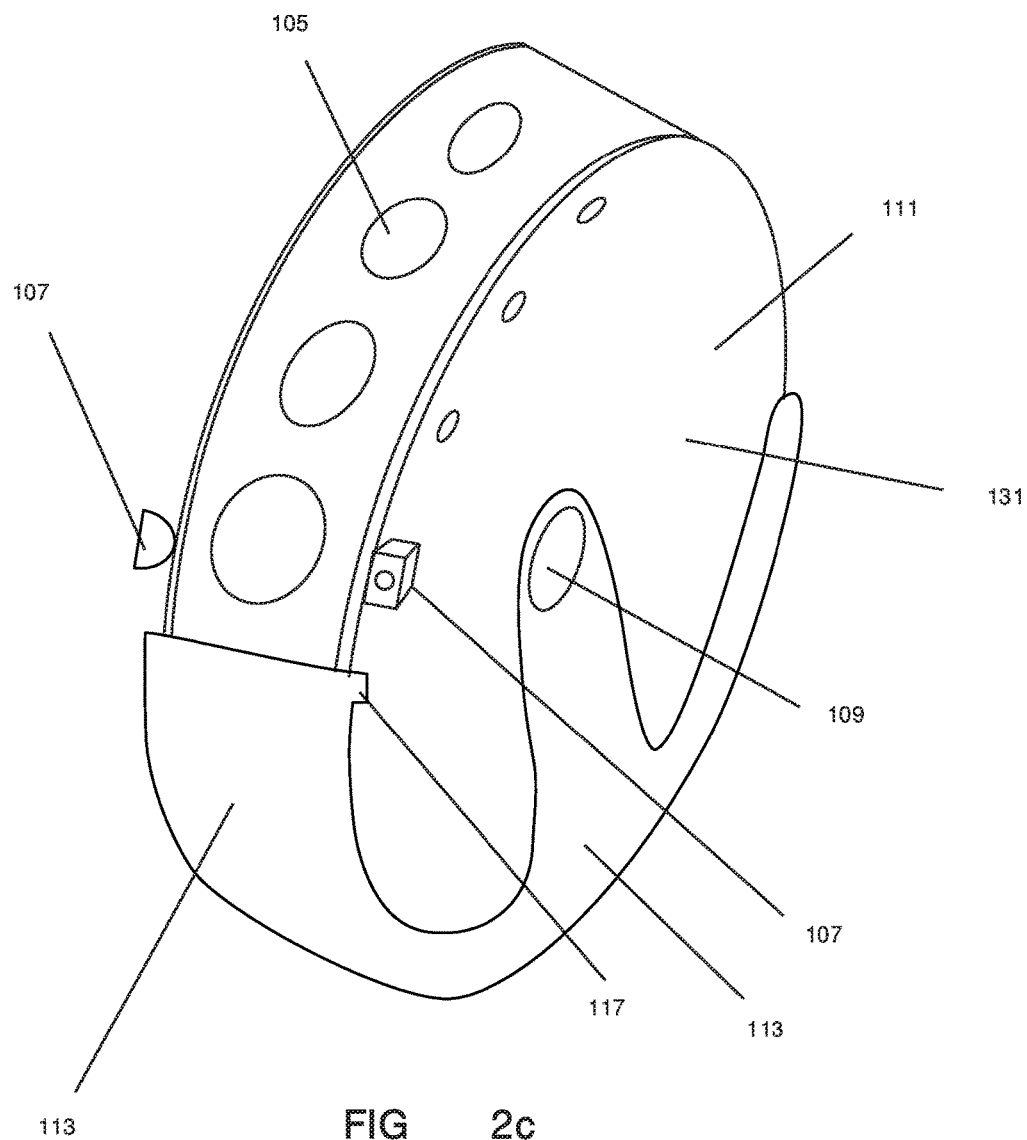
FIG. 2c shows a dosage form receiving and extracting mechanism with a series of holes in the rotating disc and shows a rotating rim.

The pill receiving and extracting mechanism (111), shown in FIG. 2c, has a rotating rim (113). Disk (131) has a series of holes (105) sized from small to big into which a single dosage form will enter when the disk (131) is rotated from behind the rim (113) serially exposing holes (105) from the smallest hole (105) to the biggest hole, (shown in FIG. 2c) of a particular bulk storage single container (103). When the hole (105) is larger than the dosage form, a dosage form will enter the hole (105). As soon as a dosage form is detected by electronic means (107) the rim (113) is rotated in the reverse direction closing off all the holes (105), preventing an additional dosage form from entering a hole (105) and allowing the disk (131) to rotate freely and unhindered by additional dosage forms to bring the dosage form trapped in hole (105) opposite funnel (190) and deposit the dosage form in funnel (190). (as shown in FIG. 2b) causing the dosage form to fall through the chute (176) into the dosage form dispensing receptacle (114). The dosage form is further advanced into the hole (105) by vibrating the receiving and extracting mechanism (111).

Figure 2D:
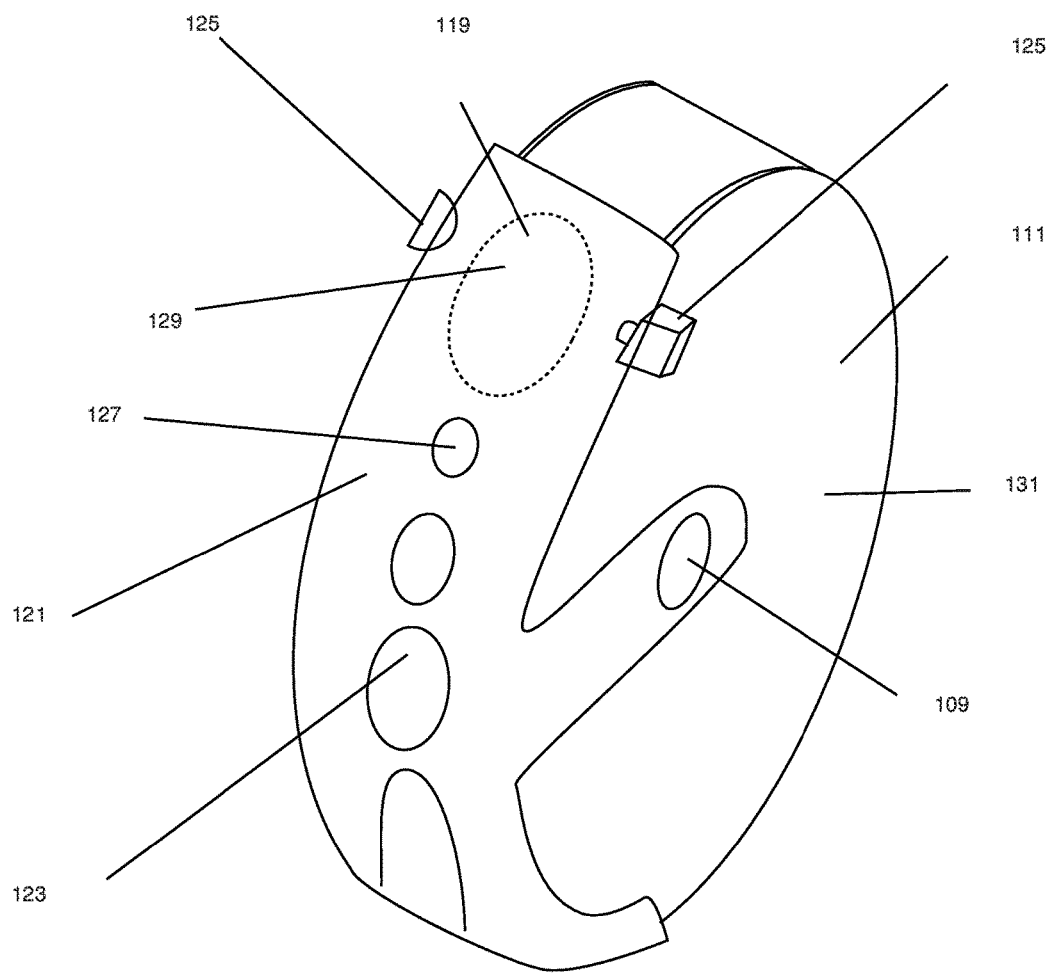
FIG. 2d shows a dosage form receiving and extracting mechanism with a rotating rim provided with a series of holes.

In a further embodiment of the receiving and extracting mechanism (111), the dosage form receiving and extracting mechanism (111), also shown in FIG. 2d, has a rotating rim (121) provided with a series of holes (123) sized from small to big into which a single dosage form will enter when the rim (121) is rotated in proximity to exit aperture cavity (119), (shown in FIG. 2d with dashed line as it is below rim (121)) of a particular bulk storage single container (103). As the rim (121) rotates, smallest hole (127) is exposed first and the hole size increases as the rim (121) advances. When the hole (123) is larger than the dosage form, a dosage form will enter the hole (123). Fixedly positioned below the rim (121) is an exit aperture cavity (119) which has a trap door (129). As soon as a dosage form is detected by electronic means (125) the rim (121) is rotated in the reverse direction closing off exit aperture cavity (119), preventing an additional dosage form from entering exit aperture cavity (119). Trap Door (129) opens, releasing dosage form into funnel (190). (as shown in FIG. 2b) causing the dosage form to fall through the chute (176) into the dosage form dispensing receptacle (114). The dosage form is further advanced into the hole (105) by vibrating the receiving and extracting mechanism (111).

A further embodiment of the receiving and extracting mechanism (111) could operate on a vacuum extractor which is extensively used in industry and will lift and transfer each independent dosage form from the aperture (115) to the funnel (190).

Figure 1B:
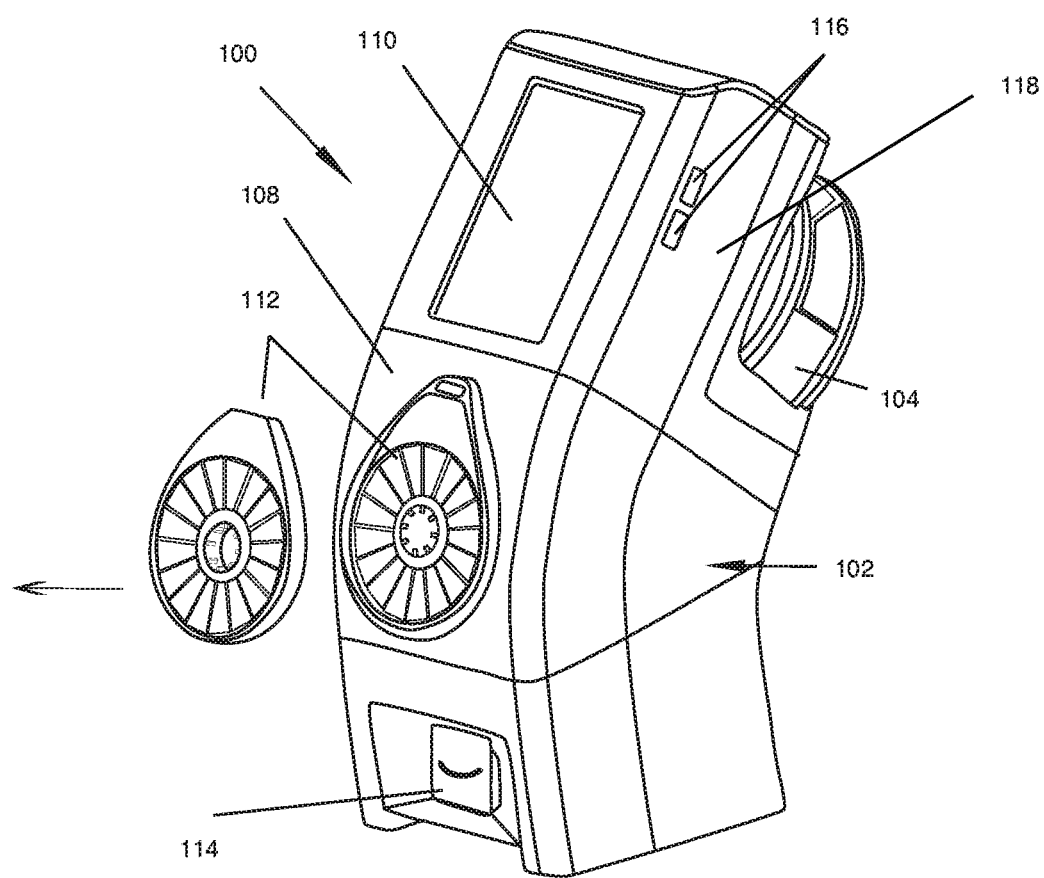
FIG. 1b shows a front perspective view of an assembled controlled dosage form-dispensing system of the present invention.

If a further embodiment as in FIG. 1b, a portable dosage form-dispensing cassette (112) and a dispensing receptacle (114) are provided. Cassette (112) is removably attached to dispenser (102), as described herein below. Ports (116) for connecting to a control station (not shown) are situated along a first side (118) of dispenser (102). It is understood that the configuration of dispenser (102) and its components shown in the figures are according to a preferred embodiment, but may be modified in other embodiments based on factors such as manufacturing costs, as well as structural and design considerations.

Figure 3:
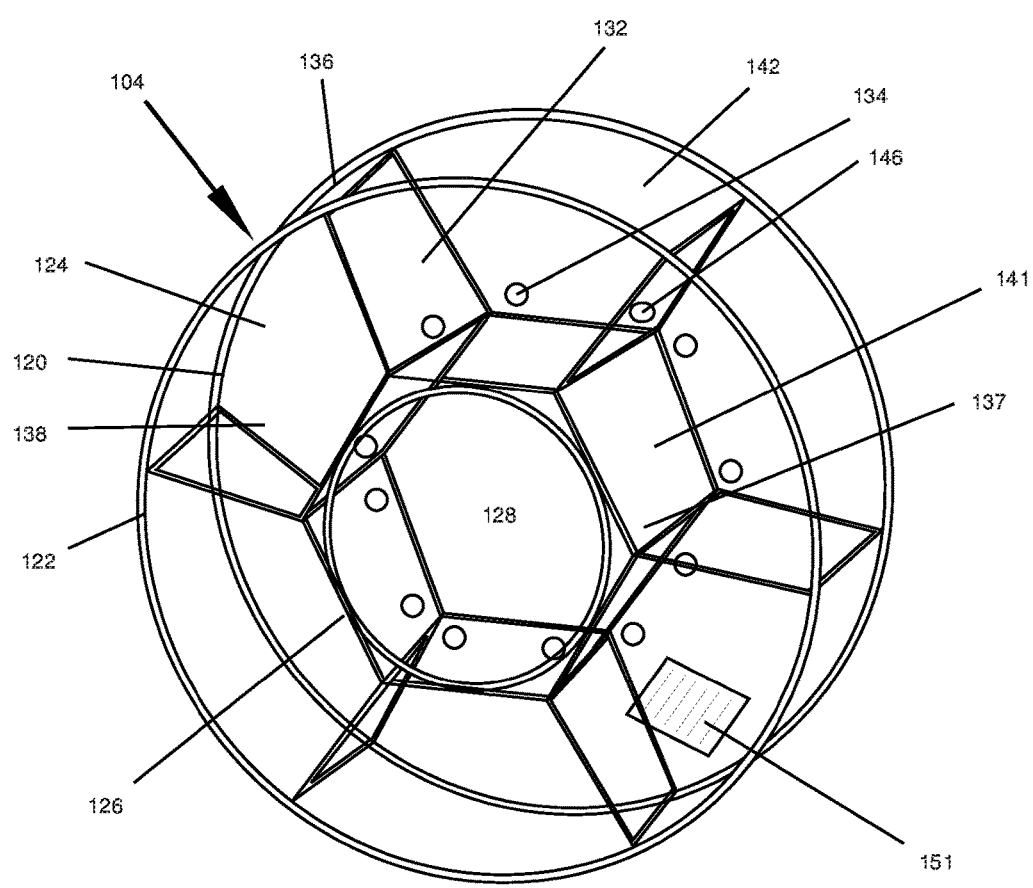
FIG. 3 shows a medicine storage and distribution unit of the present invention.
Figure 4A:
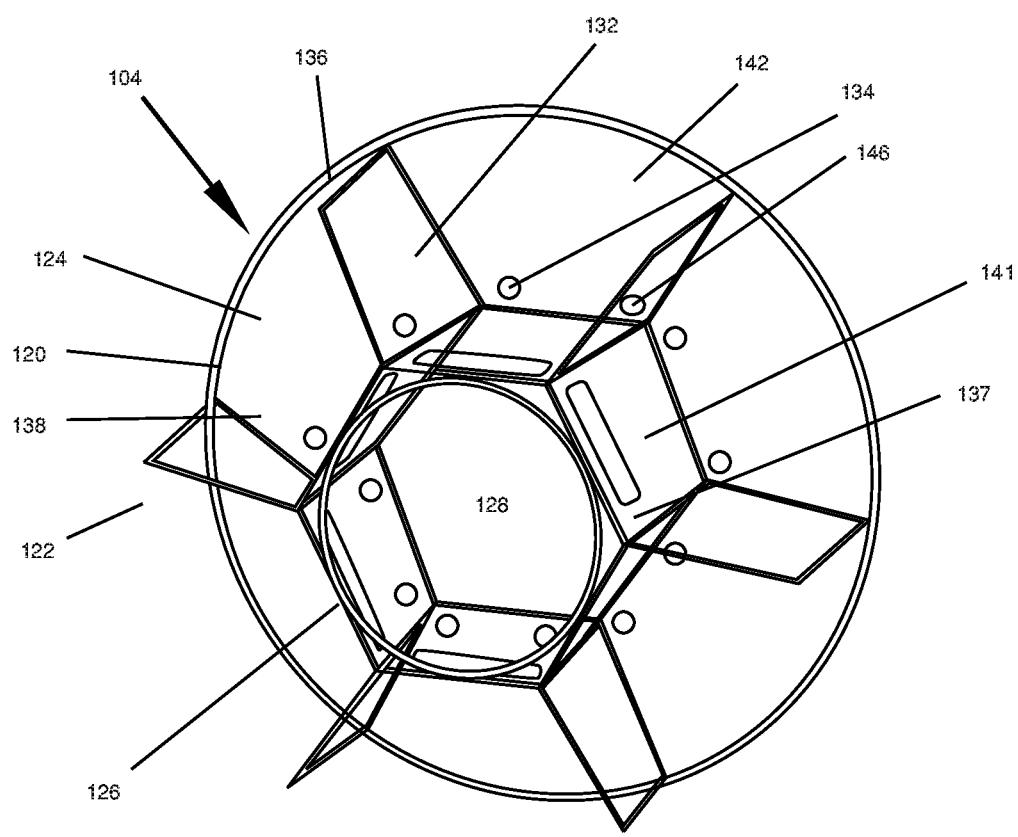
FIGS. 4a and 4b show a sectioned portion (FIG. 4a) and cover portion (FIG. 4b) of a medicine storage and distribution unit of FIG. 3.
Figure 4B:
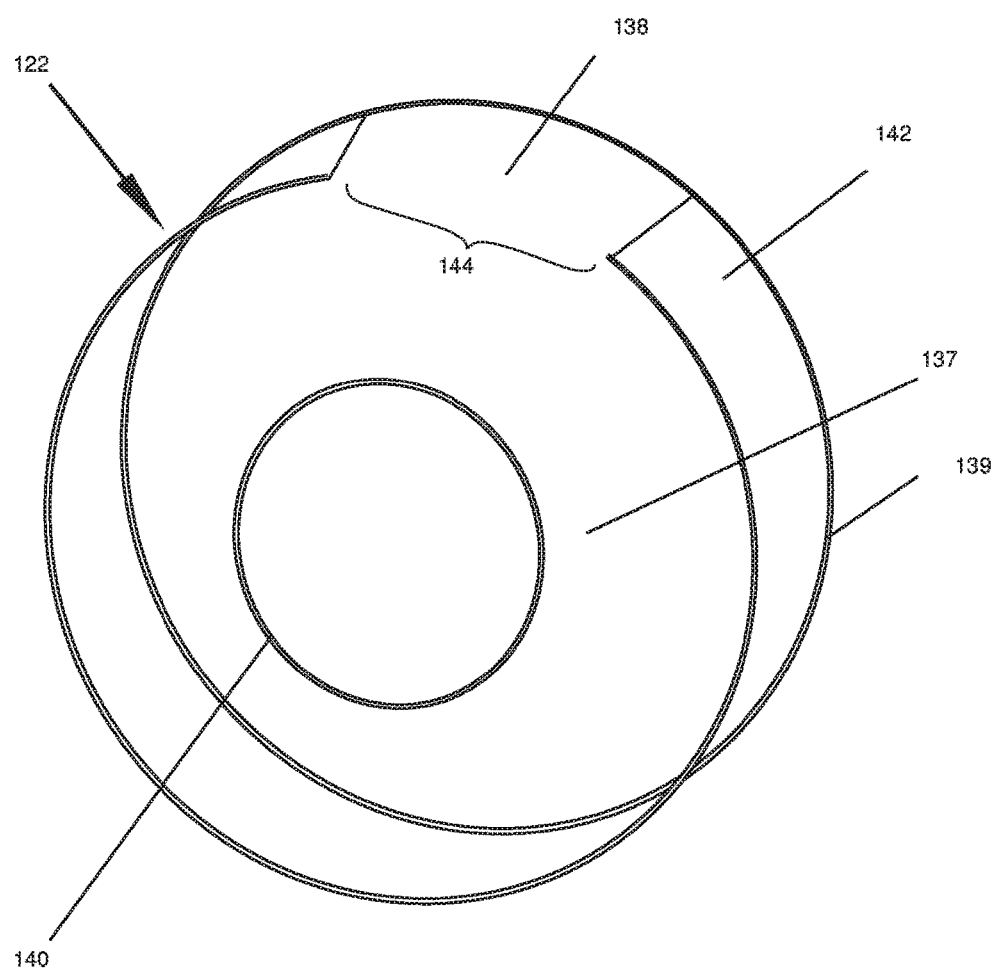

Referring to FIGS. 3, 4a and 4b, the multi-chamber, bulk medicine storage and distribution unit (104) is shown assembled (FIG. 3) in the shape of a wheel, and disassembled into sectioned portion (120) (FIG. 4a) and cover portion (122) (FIG. 4b). With reference to FIG. 4a, sectioned portion (120) comprises a disc base (124) having a central hexagonal hollow extension (126), extending orthogonally from disc base (124), forming opening (128) into which a shaft (not shown in this figure) is inserted, in order to rotate unit (104), as described herein below. A ring (130) for coupling with cover portion (122), is situated within central hexagonal extension (126), at the distal edge (131) of hexagonal extension (126). Partition walls (132) extend radially from the corner edges (134) of hexagonal extension (126) until outer edge (136) of disc base (124). With reference to FIG. 4b, cover portion (122) comprises a disc base (138) having a central cylindrical extension (140) for coupling with ring (130) of sectioned portion (120) (FIG. 4a), and an outer cylindrical wall (142) extending orthogonally from outer edge (139) of disc base (138). A gap (144) in outer cylindrical wall (142) is formed to enable a pre-packaged dosage form storage container (148) (see FIG. 5a) to be removed and replaced within storage and distribution unit (104), as described herein below. When assembled, sectioned portion (120) and cover portion (122) are rotatably connected via ring (130) and central cylindrical extension (140), such that each portion (120), (122) may be rotated independently of the other. Storage and distribution unit (104) may be disposable or reusable.

When unit (104) is assembled, as seen in FIG. 3, a plurality of individual chambers are formed between adjacent partition walls (132) and the surrounding walls of storage and distribution unit (104). Specifically, the walls of the individual hexagonal chambers include the base (146) between two adjacent partition walls (132), the wall of disc base (124) of sectioned portion (120), the wall of disc base (138) of cover portion (122), and outer cylindrical wall (142).

Figure 5A:
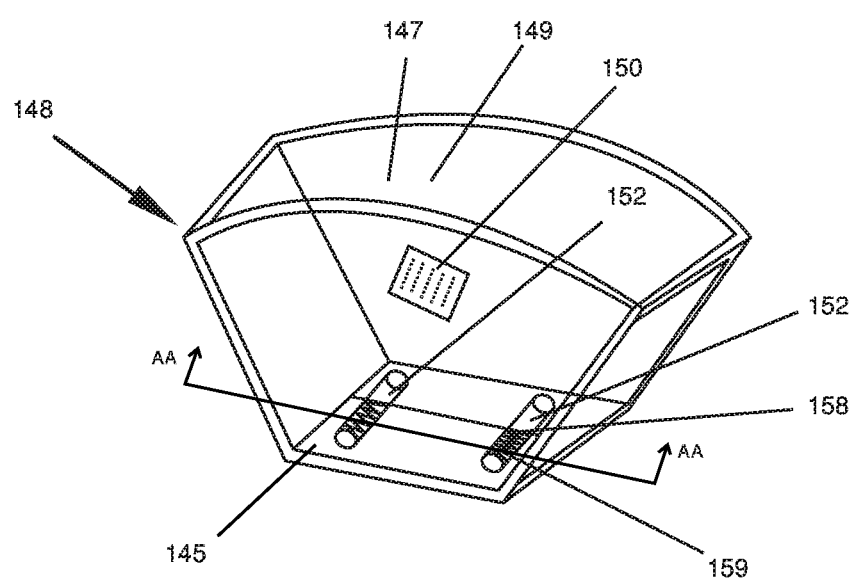
FIG. 5a shows a single container for disposing within a chamber of a medicine storage and distribution unit.

In FIG. 5a, a disposable pre-packaged dosage form storage container (148) is shown. Alternatively, container (148) is reusable. Container (148) is provided to the user as a pre-packaged dosage form storage package that is locked once filled, and only unlockable within dispenser (102). Each container (148) comprises a multiplicity of a single type of dosage forms (not shown).

Container (148) has a truncated wedge shape in order to install container (148) within a chamber of storage and distribution unit (104). Gap (144) in outer cylindrical wall (142) is slightly larger than the curved wall (149) of container (148) such that container (148) may be selectively inserted and removed from a desired chamber compartment, described herein below. As seen in FIG. 5a, an RFID tag (150) is situated on any wall of each container (148) for storing data related to the medicine contained therein. As well, as shown in FIG. 3, an RFID tag (151) is situated on storage and distribution unit (104) when assembled. Tag (151) has a range of 20-40 cm and can be situated anywhere on storage and distribution unit (104) for communication with an electronic reader.

Referring still to FIG. 5a, two channels (152) run through container (148) from a first trapezoidal face (145) toward a second trapezoidal face (147) of container (148), for receiving securing pins (154) (see FIG. 7) to lock container (148) within storage and distribution unit (104) as well as to unlock and open door (155) (see FIG. 5b) via projections (158) and spring (159) when medicine storage and distribution unit (104) is installed within dispenser (102), as described herein below. Both the storage and distribution unit (104) and each container (148) are constructed preferably of a transparent material to enable the user to view the contents of container (148).

Figure 5B:
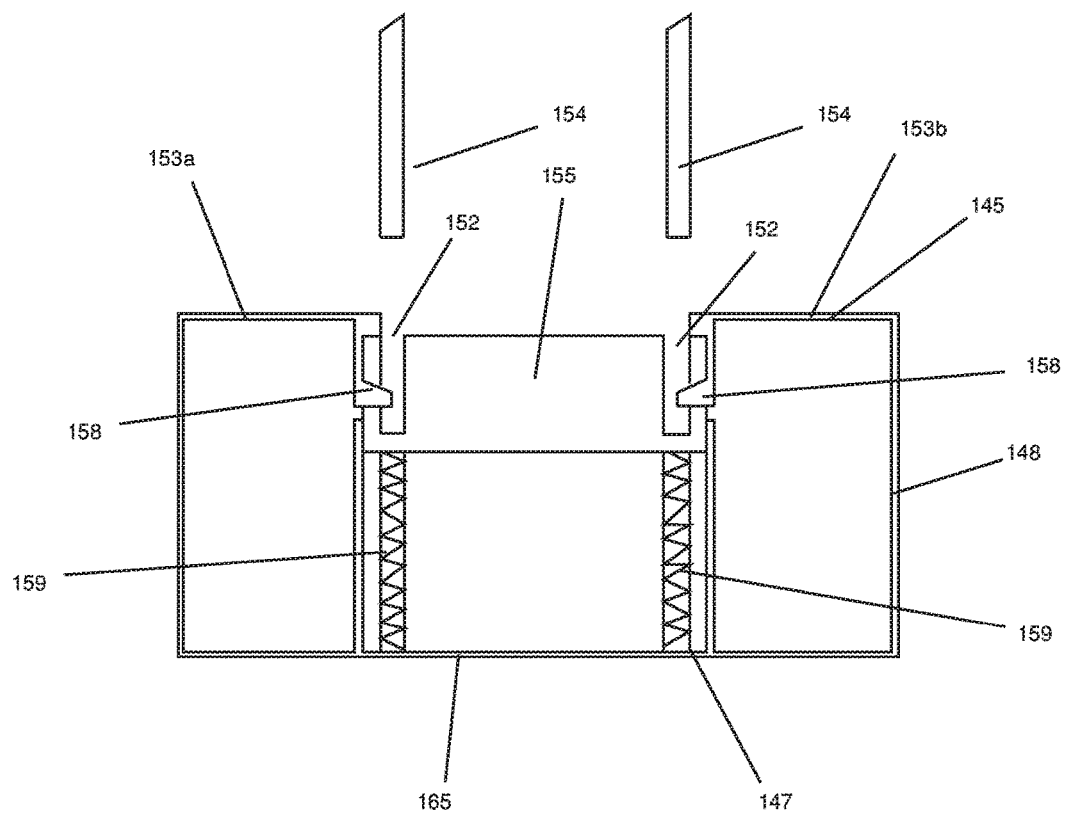
FIG. 5b shows a cross sectional view of a container of FIG. 5a, showing the door opening mechanism.

With reference to FIG. 5b, showing a cross-sectional view of container (148) cut along A-A of FIG. 5a, door (155) is shown in the normally closed position, along with a portion of side walls (153a), (153b) of container (148). Securing pins (154) are positioned out of channels (152) for illustrative purposes. As described below, securing pins (154) pass through openings (137) in disc base (124) of cover portion (120) (see FIGS. 3 and 4a), and enter into channels (152), thereby securing container (148) within storage and distribution unit (104). Projections (158) extend from the edges of side walls (153a), (153b) of container (148) through apertures (157) and into channels (152), for locking door (155) in a closed position. In order to shift door (155) to an open position for allowing the medicine contained within container (148) to exit therefrom, securing pins (154) are inserted further into channels (152) and push projections (158) out of channel (152), thereby allowing door (155) to be slidingly, shiftable. After projections are pushed out of channels (152), pins (154) are inserted further into channels (152) and force the base (163) of door (155) toward edge (165), thereby compressing springs (159). Medicine may then be removed from compartment (148) via the opening formed when door (155) is in the open position (not shown.)

In order to return door (155) to the normally closed and locked position, securing pins (154) are removed from channels (152), and springs (159) force door (155) back to the normally closed position. Projections (158) enter channels (152) thereby locking door (155) in the normally closed position.

Figure 6:
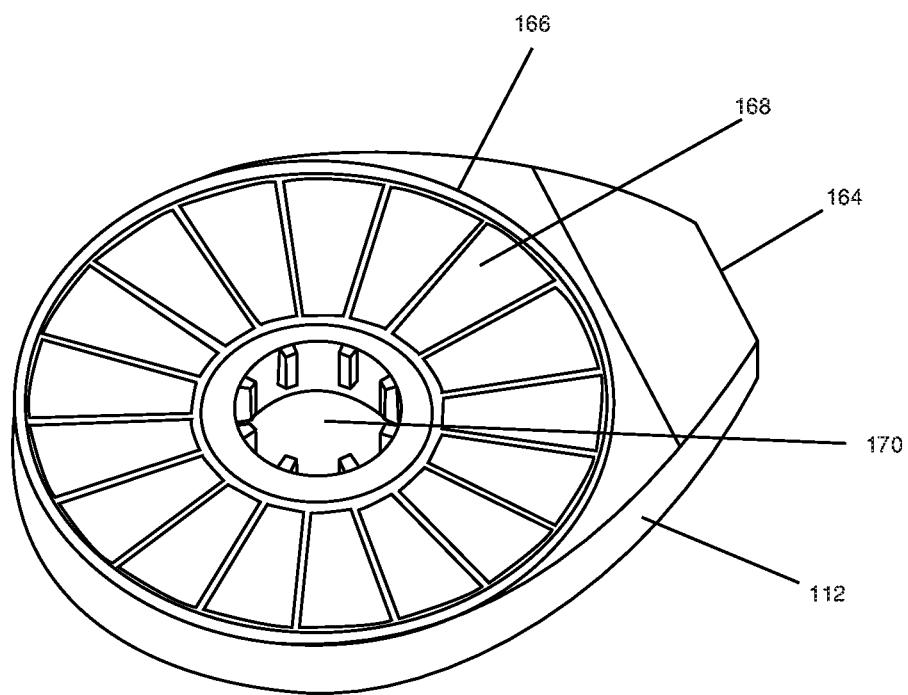
FIG. 6 shows a portable dosage form-dispensing cassette of the present invention.

FIG. 6 shows portable dosage form-dispensing cassette (112), also seen in FIG. 1 removed from dispenser (102), and comprises an outer housing (164), which is fixed in place when cassette (112) is attached to dispenser (102), and an inner housing (166), which is independently rotatable about its central axis. Inner housing (166) comprises multiple compartments (168) for accommodating medicine therein. A central opening (170) is formed at the center of cassette (112), into which a rotating shaft (not shown in this figure) is inserted when cassette (112) is attached to dispenser (102), as described herein below.

Figure 7:
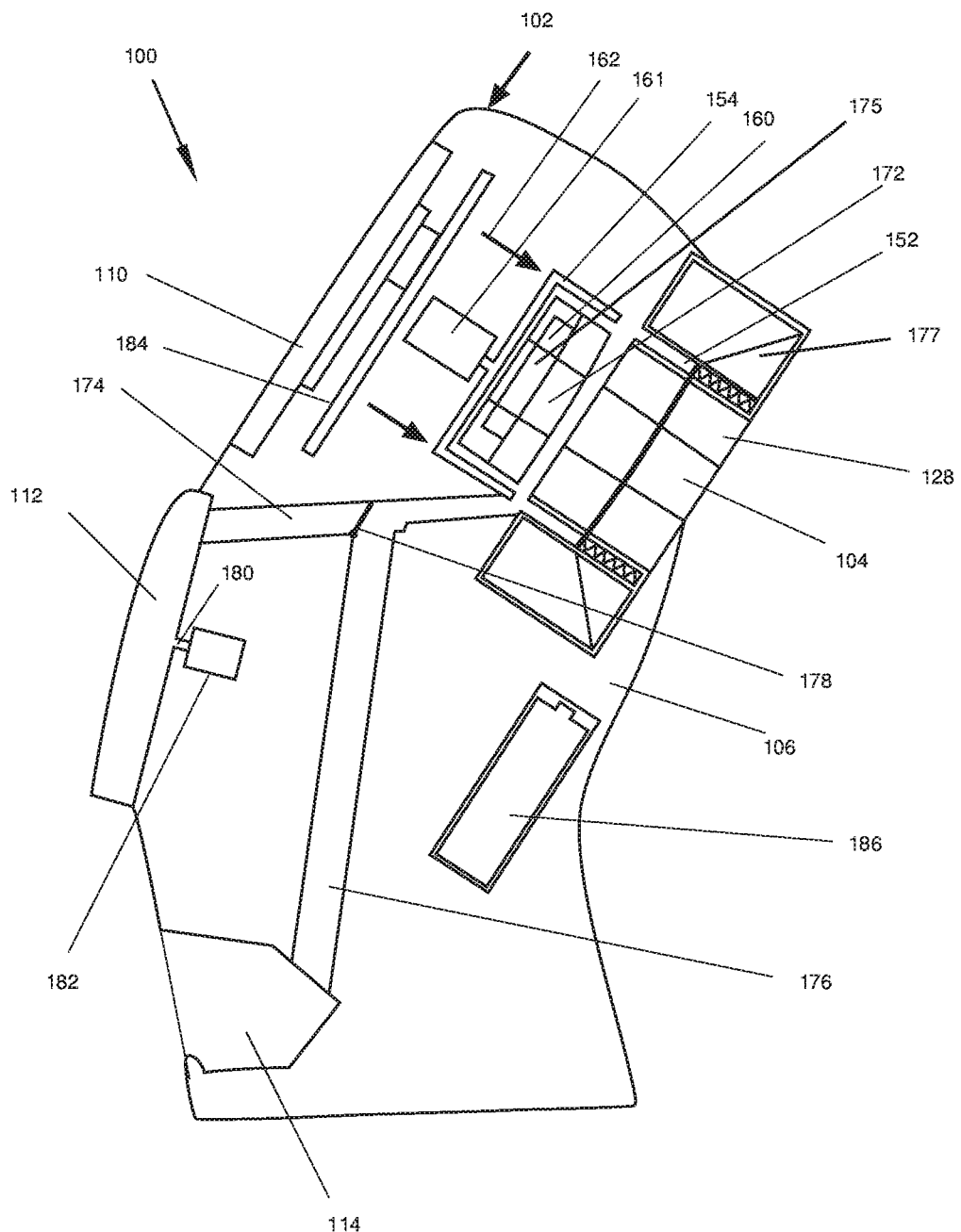
FIG. 7 shows schematically, a personal medication dispenser and its components, longitudinally cross sectioned, such that the internal components of the dispenser are seen.

Referring to FIG. 7, controlled dosage form-dispensing system (100) is shown schematically, longitudinally cross sectioned, such that dispenser (102) and its internal components are seen. When storage and distribution unit (104) is installed within dispenser (102), driving and rotating mechanism (160) shifts in the direction of arrows (162) such that shaft (172) is disposed within opening (128) of storage and distribution unit (104), and securing pins (154) pass through openings (137) in disc base (124) of cover portion (120) (see FIGS. 3 and 4a), and enter into channels (152). Preferably, the shifting of driving and rotating mechanism (160) is automated, however the user may selectively shift driving and rotating mechanism (160) manually.

Gap (144) in outer cylindrical wall (142) (FIG. 4b, not seen in FIG. 7) is normally disposed downward, toward the inside of dispenser (102) after container (148) is installed therein, to cover moving parts and thus prevent injury to user. When it is desired to replace an empty container with a container containing dosage forms, cover portion (122) (FIG. 4b) is rotated, either manually or by motor (161), around its central axis such that gap (144) is positioned upward, toward the outside of dispenser (102) to allow a container (148) to be removed from storage and distribution unit (104) via gap (144). In a preferred embodiment, when motor (161) turns in one direction it rotates storage and distribution unit (104); when it turns in the opposite direction it rotates cover portion (122) Following the replacement with a new container (148), cover portion (122) is then rotated back to its normal orientations such that gap (144) is disposed toward the inside of dispenser (102).

When it is time to administer a dosage form, driving and rotating mechanism (160) moves in the direction of arrows (162) and enters and engages into opening (128) and rotates sectioned portion (120) via motor (161) to align the container (148) from which a dosage form is to be removed, with the dosage form receiving and extracting mechanism (175). The door of container (177) is now opened as described previously and a dosage form from container (177) can now enter via the open container door into the extracting mechanism (175) which is now aligned with the open container door. Securing pins (154) unlock the chamber door (155) (see FIG. 5b) as described above, and a predetermined number of dosage forms are extracted from container (148) through opening (141) in hexagonal extension (140) and transferred to a first, main chute (174) for directing the pill or dosage forms to either portable cassette (112), or alternatively, to a second, branch chute (176) for directing the dosage form or dosage forms to dispensing receptacle (114). A diverter valve comprising a pivoting hatch (178) is situated at the junction of first and second chutes (174), (176), and selectively opens and closes the desired chutes (174), (176) for diverting the dosage form or dosage forms to the suitable chute (174), (176) depending on the desired final location of the pill or dosage forms The receptacle (114) is a container with or without a manual door into which the dosage form falls and can be removed manually.

Shaft (180), extending from motor (182) is inserted into central opening (170) (See FIG. 6) of portable cassette (112) for rotating cassette (112) such that a desired compartment (168), for instance, if it is empty or low on dosage forms, is aligned with first chute (174) in order to receive a pill or dosage forms from storage and distribution unit (104) when needed.

Also shown in FIG. 7 is display screen (110) and a printed circuit board with microprocessor (184). A power source comprising a battery pack (186) is positioned at back wall (106) of dispenser (102). Battery pack (186) may be of the rechargeable type.

In order to operate system (100) of the present invention, medication dispenser (102) is preprogrammed at a hospital, doctor's office, pharmacy or by any authorized healthcare professional at the home of the patient to dispense medication at predetermined times and amounts. Dispenser (102) is provided with wireless communication means, or alternatively, wired communication means via ports (116) on side (118) of dispenser for communicating with a control center and/or with a cloud-based network. In one aspect display screen (110) functions solely as a panel for providing to the user relevant data such as: type of medication currently in dispenser (102), time of next medication release, etc., but does not enable an authorized user to program system (100) therefrom. In another aspect, display screen (110) functions as well as a controller for enabling an authorized user to program system (100) therefrom. Display screen (110) additionally provides a visual indicator to the user to alert him to take the medication. Additionally or alternatively, other alerting means, such as audio, may be used to remind the user to take the medication.

Figure 8:
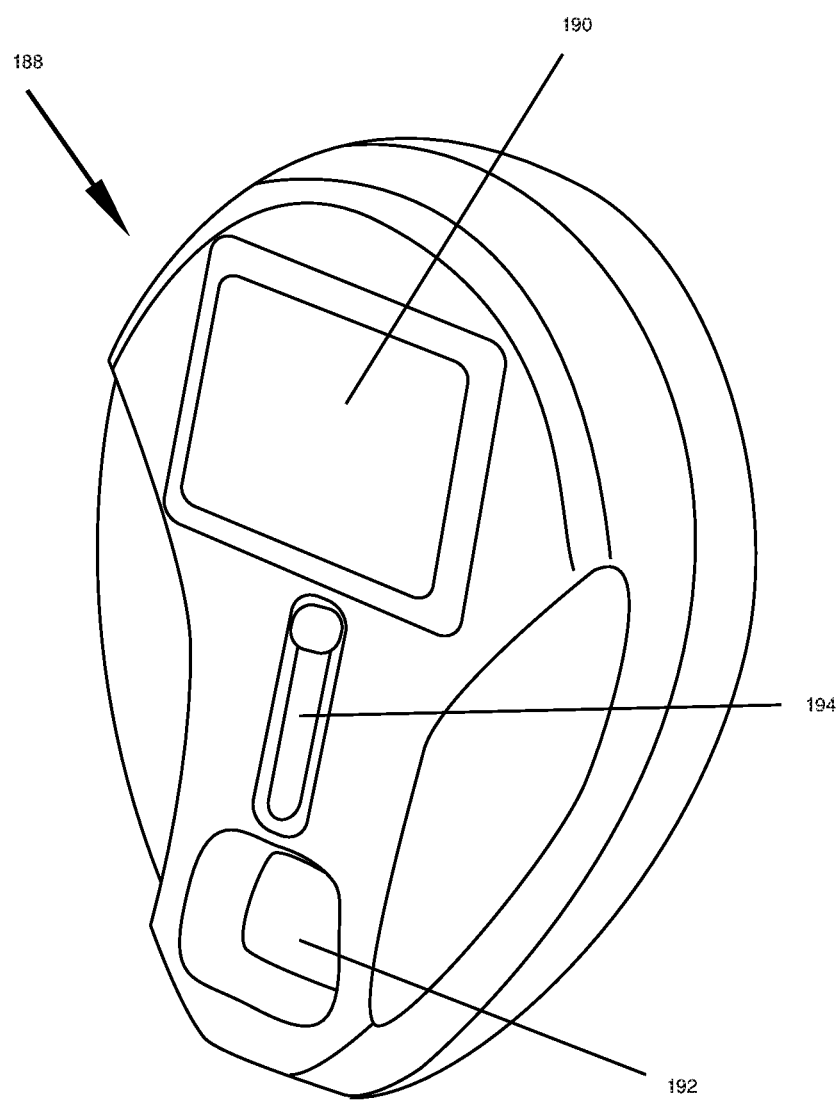
FIG. 8 shows a front view of a pocket dispenser of the present invention.
Figure 9:
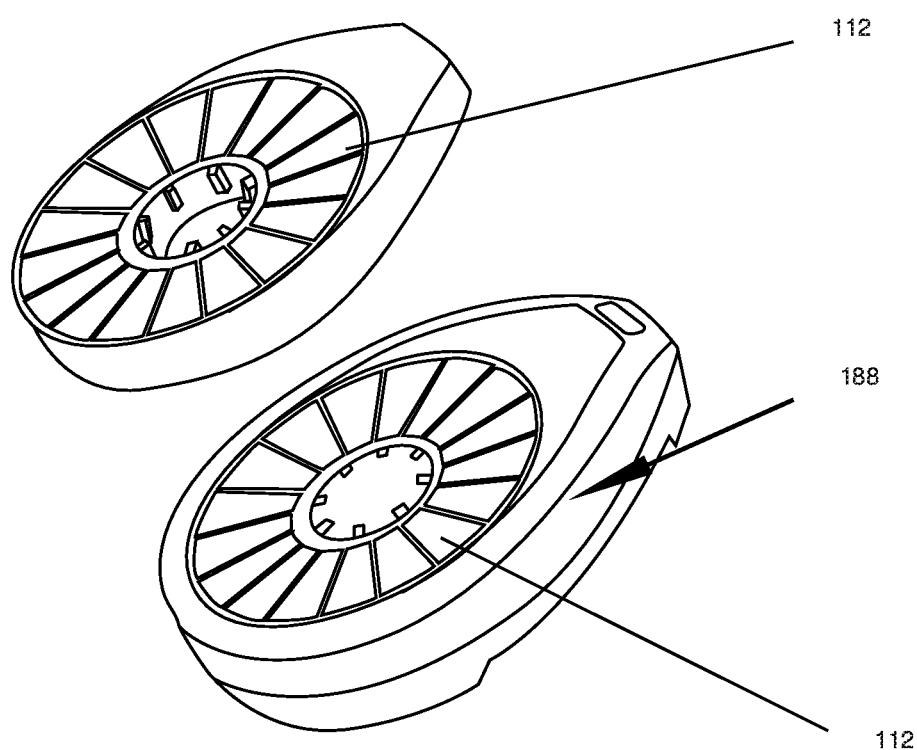
FIG. 9 shows a back view of a portable pocket dispenser of FIG. 8, with a portable dosage form-dispensing cassette secured therein as well as detached therefrom.

The controlled dosage form-dispensing system (100) of the present invention further comprises a pocket dispenser (188) shown in a front perspective view in FIG. 8, and in a back view in FIG. 9, showing cassette (112) both within pocket dispenser (188) and removed therefrom. Pocket dispenser (188) is shown comprising an LCD display screen (190) (although in some embodiments screen (190) is not present), a receptacle (192) for receiving dosage forms removed from cassette (112) and a dosage form releasing mechanism (194) for removing dosage forms from a cassette compartment (168) and transferring to receptacle (192 In a preferred embodiment this will be manually operated. Pocket dispenser (188) comprises the same essential features as that of the home medication dispenser described herein above, mutatis mutandis, such as requiring an authorized user to program the times of dispensing, the number of dosage forms, etc. According to one aspect, portable pocket dispenser (188) is disposable, and according to another aspect, pocket dispenser (188) is reusable.

It should be noted that the terms, "medicine" and "pill" and "dosage form" and grammatical forms thereof are used interchangeably herein, and refer to any form of solid medicament, including tablets, caplets, and capsules and others.

It is understood that the above description of the embodiments of the present invention are for illustrative purposes only, and is not meant to be exhaustive or to limit the invention to the precise form or forms disclosed, as many modifications and variations are possible. Such modifications and variations are intended to be included within the scope of the present invention as defined by the accompanying claims.

What is claimed is:

1. A controlled dosage form-dispensing device, comprising:

a. a multi-chamber, bulk medicine storage and distribution unit, wherein said unit is provided with a plurality of individual dosage form-containing storage chambers with respective delivery ports;

a personal medication dispenser comprising:
    a fixed dosage form extracting station comprising a dosage form receiving and extracting mechanism; and
    a pair of chutes to receive and deliver the dosage form to either at least one portable dosage form-dispensing cassette or to a dispensing receptacle, said chutes being selectively opened and closed by a pivoting hatch;

wherein said personal medication dispenser is provided with a controller which moves said bulk medicine storage and distribution unit sequentially bringing said respective delivery port of a predetermined chamber into register with said fixed dosage form extracting station such that said dosage form receiving and extracting mechanism extracts and receives only one dosage form at a time;

c. the at least one portable dosage form-dispensing cassette having a plurality of compartments and a first delivery controller for delivery of a predetermined dosage form from a predetermined compartment of said portable dosage form-dispensing cassette, said at least one portable dosage form-dispensing cassette being releasably attachable to the personal medication dispenser; and d. a second delivery controller for the controlled delivery of predetermined dosage forms from said multi-chamber, bulk medicine storage and distribution unit to said portable dosage form-dispensing cassette via one of said chutes.

2. A controlled dosage form-dispensing device according to claim 1, wherein each chamber is sized to receive and engage individual drug distributor issued, pre-packaged dosage form storage containers.

3. A controlled dosage form dispensing device of claim 2, wherein said individual drug distributor issued, prepackaged dosage form storage containers are locked once filled, and are unlockable only within said personal medication dispenser.

4. A controlled dosage form dispensing device of claim 1, wherein said device is provided with a portable pocket dispensing unit into which said portable dosage form-dispensing cassette is inserted.

5. A controlled dosage form dispensing device of claim 4, wherein said portable pocket dispensing unit is in wireless communication with a network.

6. A controlled dosage form dispensing device of claim 1, wherein said device dispenses drugs and provides any one of an audio, visual and radio communication signal to a user according to the information received from a RFID tag.

7. A controlled dosage form dispensing device of claim 1, wherein said portable dosage form-dispensing cassette is disposable.

8. A controlled dosage form dispending device of claim 1, wherein said personal medication dispenser comprises a rotator which rotates said multi-chamber, bulk medicine storage and distribution unit.

9. A controlled dosage form dispensing device of claim 1, wherein each chamber accommodates or contains a multiplicity of a single type of dosage form.

10. A controlled dosage form dispensing device of claim 1, wherein said multi-chamber, bulk medicine storage and distribution unit is removable from said personal medication dispenser for external prepackaging of drug distributor issued dosage forms.

11. A controlled dosage form dispensing device of claim 1, wherein said personal medication dispenser comprises a conduit for the controlled delivery of predetermined dosage forms from said multi-chamber, bulk medicine storage and distribution unit to a dispensing receptacle for receiving a pill from said channel and dispensing the same.

12. A controlled dosage form dispensing device of claim 1, wherein said personal medication dispenser is in communication with said portable dosage form-dispensing cassette, said portable dosage form-dispensing cassette having an RFID tag for storing information related to the cassette contents.

13. A controlled dosage form dispensing device of claim 1, wherein said multi-chamber, bulk medicine storage and distribution unit is removable and disposable.

14. A controlled dosage form dispensing device of claim 1, wherein said individual chambers are disposable.

15. A controlled dosage form dispensing device of claim 1, wherein said personal medication dispenser is in wireless communication with a network.

\* \* \* \* \*